United States Patent [19]

Balkenhohl et al.

[11] Patent Number: 5,530,143
[45] Date of Patent: Jun. 25, 1996

[54] PREPARATION OF (6S)-6,8-DIHYDROXYOCTANOIC ESTERS

[75] Inventors: Friedhelm Balkenhohl, Limburgerhof; Joachim Paust, Neuhofen, both of Germany

[73] Assignee: BASF Aktiengesellschaft, Ludwigshafen, Germany

[21] Appl. No.: 381,424

[22] Filed: Jan. 31, 1995

Related U.S. Application Data

[63] Continuation of Ser. No. 795,157, Nov. 20, 1991, abandoned.

[30] Foreign Application Priority Data

Nov. 24, 1990 [DE] Germany .................. 40 37 440.8

[51] Int. Cl.⁶ .................. C07D 339/04; C07C 69/66
[52] U.S. Cl. .................. 549/39; 560/145; 560/180
[58] Field of Search .................. 560/145, 180; 549/39

[56] References Cited

U.S. PATENT DOCUMENTS

| | | | |
|---|---|---|---|
| 2,875,227 | 2/1959 | Walton et al. | 549/39 |
| 2,875,238 | 2/1959 | Holly et al. | 549/39 |
| 4,772,727 | 9/1988 | Sutherland et al. | 549/39 |
| 4,966,732 | 10/1990 | Giray et al. | 549/39 |

FOREIGN PATENT DOCUMENTS

| | | | |
|---|---|---|---|
| 384189 | 8/1990 | European Pat. Off. | 560/179 |
| 3629116 | 3/1985 | Germany | 589/39 |

OTHER PUBLICATIONS

Brookes et al. J. Chem. Soc. Perkin Trans. I (1988), pp. 9–12.
Gopalan et al, "Stereochemical Control of Yeast Reductions: Synthesis of R–(+)–α–Lipoic Acid," Tet. Lett., vol. 30, No. 42, pp. 5705–5708, (1989).
E Jellum et al., *Biomedical and Environmental Mass Spectrometry*, vol. 16, pp. 57–62 (1988).
J. Svendsen et al., (I), *Organic Mass Spectrum*, vol. 22, No. 7, pp. 421–429 (1988).
J. Svendsen et al., (II), *Chromatography and Mass Spectrometry in Nutrition Science and Food Safety*, pp. 223–234, Elsevier Science (1984).
F. Carey et al., "Advanced Organic Chemistry" 2nd ed., pp. 199–203, Plenum Press, New York (1983).
J. March, "Advaned Organic Chemistry" 2nd ed. pp. 829–831 McGraw–Hill Book Co., New York (1977).
Jellum et al, *Chemical Abstracts* 110:150863n, p. 384, abstract of *Biomed Environ. Mass Spectrom.* 1987 (pub 1988), 16(1–n), 57–62 (1989).
Svendsen et al. (I) *Chemical Abstracts* 109:231121a, p. 875, abstract of *Org. Mass Spectrum* 1987, 22(7), 421–9 (1988).
Svendsen et al. (II) *Chemical Abstracts* 101:208080n, p. 396, abstract of *Anal. Chem. Symp. Ser.* 1984, 223–34 (1984).
J March, "Advanced Organic Chemistry" 3rd ed. pp. 104–107, John Wiley & Sons, N.Y. (1985).

*Primary Examiner*—Allen J. Robinson
*Assistant Examiner*—Mary C. Cebulak
*Attorney, Agent, or Firm*—Keil & Weinkauf

[57] ABSTRACT (6S)-6,8-Dihydroxyoctanoic esters I

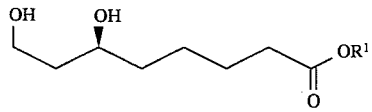

($R^1$=alkyl, cycloalkyl, aralkyl or aryl), are prepared by reducing a (3S)-3-hydroxyoctanedioic diester II

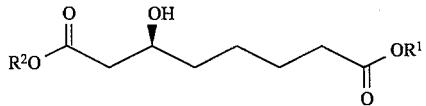

($R^2$=an $R^1$ radical group) with a complex hydride and are mainly used as intermediates for synthesizing compounds of the type of liponic acid.

7 Claims, No Drawings

PREPARATION OF (6S)-6,8-DIHYDROXYOCTANOIC ESTERS

This application is a continuation of application Ser. No. 07/795,157, filed on Nov. 20, 1991, now abandoned.

The present invention relates to a novel process for preparing (6S)-6,8-dihydroxyoctanoic esters of the formula I

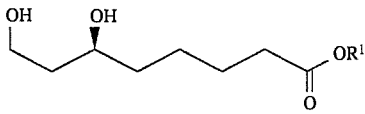

where $R^1$ is alkyl, cycloalkyl, aralkyl or aryl.

The present invention also relates to a process for preparing (3S)-3-hydroxyoctanedioic diesters.

The invention additionally relates to novel (3S)- 3-hydroxyoctanedioic diesters and novel 3-oxooctanedioic diesters, and to a process for preparing R-(+)-α-liponic acid.

The compounds I are known and are used as intermediates for the synthesis of enantiomerically pure R-(+)-α-liponic acid (thioctic acid).

J. Chem. Soc. Perkin Trans. I (1988) 9 describes the preparation thereof from the malic acid derivative (S)-4-phenylmethoxy-1,2-butanediol by a multistage reaction sequence with the intermediates (R)-4-phenylmethoxy- 1,2-butanediol, (R)-(2-phenylmethoxyethyl)oxirane, 6-hydroxy-8-(phenylmethoxy)-l-octene to give methyl (6S)-6,8-dihydroxyoctanoate.

Tetrahedron Letters, 42 (1989) 5705 discloses the alkylation of the bisanion of acetoacetic ester to give 3-oxo-7-cyanoheptanoic ester, the reduction thereof with baker's yeast to (3S)-3-hydroxy-7-cyanoheptanoic ester, subsequent reduction of this compound with lithium borohydride in tetrahydrofuran, and alcoholysis to give ethyl (6S)-6,8-dihydroxyoctanoate. The preparation of R-(+)-α-liponic acid is also described in this reference. Another possible synthesis of R-(+)-α-liponic acid is the multistage conversion of propargyl alcohol via the intermediates E-2,8-nonadien-1-ol,2S,3S-epoxy-1-hydroxy- 8-nonene, 1,3-dihydroxy-8-nonene, 1,3-disulfoxy-8-nonene and 6,8-disulfoxyoctanoic acid (DE-A 36 29 116).

However, the processes disclosed to date are unsatisfactory, despite high chemical yields, because of the great industrial elaboration and of the inadequate optical purity.

It is an object of the present invention to make the (6S)-6,8-dihydroxyoctanoic esters I available in high optical and chemical yield in a more straightforward and economic manner, and to provide further starting materials for this purpose.

We have found that this object is achieved by a novel process for preparing (6S)-6,8-dihydroxyoctanoic esters of the formula I

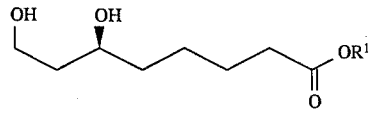

where $R^1$ is alkyl, cycloalkyl, aralkyl or aryl, which comprises reducing a (3S)-3-hydroxyoctanedioic diester of the formula II

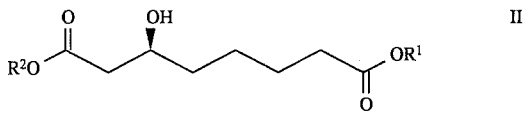

where $R^2$ is one of the $R^1$ radicals, with a complex hydride.

We have also found a process for preparing (3S)-3-hydroxyoctanedioic diesters, novel (3S)-3-hydroxyoctanedioic diesters and novel 3-oxooctanedioic diesters, and a process for preparing R-(+)-α-liponic acid.

The (3S)-3-hydroxyoctanedioic diesters II to be employed according to the invention are novel. Preferred among these compounds are those of the formula IIa where $R^{1a}$ and $R^{2a}$ have the following meanings:
$C_1$–$C_{20}$-alkyl, preferably $C_1$–$C_8$-alkyl, particularly preferably $C_1$–$C_{20}$-alkyl such as ethyl, n-propyl, iso-propyl, n-butyl, n-pentyl and especially methyl and iso-butyl;
$C_3$–$C_{12}$-cycloalkyl, preferably $C_3$–$C_8$-cycloalkyl such as cyclopropyl, cyclobutyl, cyclopentyl, cycloheptyl, cyclooctyl and especially cyclohexyl;
$C_7$–$C_{12}$-aralkyl, preferably phenylethyl and very especially benzyl;
mononuclear or binuclear aryl such as naphthyl and especially phenyl.

The alkyl, cycloalkyl, aralkyl and aryl groups in turn can carry preferably up to 2 substituents, especially $C_1$–$C_{12}$-alkyl, $C_1$–$C_{12}$-alkoxy and halogen.

Preferred starting materials II are:
dimethyl (3S)-3-hydroxyoctanedioate
1-ethyl 8-methyl (3S)-3-hydroxyoctanedioate
8-methyl 1-propyl (3S)-3-hydroxyoctanedioate
8-methyl 1-iso-propyl (3S)-3-hydroxyoctanedioate
1-butyl 8-methyl (3S)-3-hydroxyoctanedioate
1-sec-butyl 8-methyl (3S)-3-hydroxyoctanedioate
8-methyl 1-tert-butyl (3S)-3-hydroxyoctanedioate
8-methyl 1-octyl (3S)-3-hydroxyoctanedioate
8-methyl 1-phenyl (3S)-3-hydroxyoctanedioate
1-(2-ethylhexyl) 8-methyl (3S)-3-hydroxyoctanedioate.

With a view to the required products I, 1-isobutyl 8-methyl (3S)-3-hydroxyoctanedioate is particularly preferred.

The starting compounds II are reduced to the products I with a complex hydride, the molar ratio of complex hydride to II expediently being from 1:1 to 3:1, especially 1.5:1 to 2.5:1.

Preferred complex hydrides are borohydrides such as lithium and potassium borohydride and, particularly preferably sodium borohydride.

Also suitable are, in particular, alkyl- and alkoxy-substituted borohydrides such as lithium triethylborohydride and sodium trimethoxyborohydride.

It is advisable to carry out the reduction of II to I in an aprotic solvent. Suitable and preferred for this are aliphatic and aromatic hydrocarbons such as hexane, cyclohexane, toluene, benzene and xylene, and ethers such as dioxane, diethyl ether and, particularly preferably, tetrahydrofuran.

The reaction is generally carried out at from 0° to 150° C., preferably at from 25° to 70° C.

The reaction is normally carried out under atmospheric pressure, but it can also be carried out under reduced or slightly elevated pressure, ie. in the range from 0.1 to 10 bar approximately.

The reaction times are normally from 0.5 to 5 hours, usually from 1 to 2 hours.

The process is generally carried out in such a way that a solution of the starting compound II in the aprotic solvent is mixed with the complex hydride, and the resulting suspension is heated.

The reaction mixture can be worked up in a conventional manner, usually by hydrolysis, extraction and drying, to give the products I.

The starting compounds II can be prepared according to the invention from the 3-oxooctanedioic diesters III.

Those compounds III which are not known can be obtained by conventional methods, especially by acylation of Meldrum's acid with alkyl 5-chloroformylpentanoate and subsequent alcoholysis (for $R^1$ and $R^2$=methyl: Leibigs Ann. Chem. (1983) 1237; for $R^1$=methyl and $R^2$=tert-butyl: Chem. Ber., 122 (1989) 797; for $R^1$ and $R^2$=ethyl: Org. Prep. Proced. Int., 20 (1988) 184).

Novel compounds IIIb of very particular importance are those where $R^{1b}$ and $R^{2b}$ have the following meanings:

$C_1$–$C_{20}$-alkyl, excepting methyl for $R^{1b}$ and methyl or tertbutyl for $R^{2b}$, and ethyl for $R^{1b}$ and $R^{2b}$, preferably $C_1$–$C_8$-alkyl, particularly preferably $C_1$–$C_5$-alkyl such as ethyl, n-propyl, iso-propyl, n-butyl, n-pentyl and especially methyl and iso-butyl;

$C_3$–$C_{12}$-cycloalkyl, preferably $C_3$–$C_8$-cycloalkyl such as cyclopropyl, cyclobutyl, cyclopentyl, cycloheptyl, cyclooctyl and especially cyclohexyl;

$C_7$–$C_{12}$-aralkyl, preferably phenylethyl and very especially benzyl;

mononuclear or binuclear aryl such as naphthyl and especially phenyl.

The alkyl, cycloalkyl, aralkyl and aryl groups in turn can carry preferably up to 2 substituents, especially $C_1$–$C_{12}$-alkyl, $C_1$–$C_{12}$-alkoxy and halogen.

Preferred starting materials IIIb are:
1-ethyl 8-methyl 3-oxooctanedioate
8-methyl 1-propyl 3-oxooctanedioate
1-iso-propyl 8-methyl 3-oxooctanedioate
1-butyl 8-methyl 3-oxooctanedioate
8-methyl 1-sec-butyl 3-oxooctanedioate
8-methyl 1-octyl 3-oxooctanedioate
8-methyl 1-phenyl 3-oxooctanedioate
1-(2-ethylhexyl) 8-methyl 3-oxooctanedioate.

With a view to the required products I and II, 1-iso-butyl 8-methyl 3-oxooctanedioate is particularly preferred.

The compounds III are reduced to the compounds II with baker's yeast, which is preferably employed in dried form. The ratio of the amount of baker's yeast to III is expediently from 1:1 to 100:1, preferably 4:1 to 20:1.

The reduction is expediently carried out in aqueous solution.

It is advisable to add alcohols such as, preferably, ethanol or sugars to supply energy to maintain the reduction.

The reduction with baker's yeast is usually carried out at from 0° to 50° C., preferably at from 30° to 40° C.

It is expediently carried out under atmospheric pressure.

The reaction times are generally from 12 to 96 hours, usually 24 to 48 hours.

The process is normally carried out in such a way that the baker's yeast is suspended in the aqueous-alcoholic solution and, after heating, the compound III is added.

The reaction mixture is worked up in a conventional manner, usually by filtration, extraction of the filtrate and subsequent drying of the extract, to give the products II.

The compounds II are used to prepare R-(+)-α-liponic acid of the formula IV

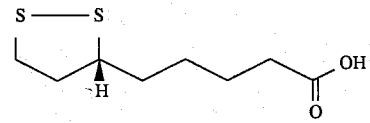

by reducing them to the compounds I and
a) converting the latter in organic solution with a sulfonyl chloride and a tertiary nitrogen base into the bissulfonic ester of I,
b) reacting this compound in a polar solvent with sulfur and an alkali metal disulfide to give an R-α-liponic ester and
c) if required converting this ester into physiologically tolerated R-(+)-α-liponic acid.

The product IV is known or can be obtained by conventional methods, especially by the reaction sequence, which has been described above, from the bisanion of acetoacetic ester to (6S)-6,8-dihydroxyoctanoic ester and its subsequent reaction via stages a, b and c (Tetrahedron Letters, 42 (1989) 5705).

The novel compounds II and the compound I prepared by the novel process usually have a high enantiomer ratio corresponding to an optical yield of from 20 to 94%.

The enantiomer ratios are measured by the method of Dale, Dull and Mosher, J. Org. Chem., 34 (1969) 2543, by gas chromatography of the diastereomeric esters of the novel alcohols and of an optically active α-methoxy-α-phenyl-α-trifluoromethylacetic acid.

The (6S)-6,8-dihydroxyoctanoic esters I prepared by the process of the invention are mainly used as intermediates for the synthesis of enantiomerically pure R-(+)-α-liponic acid. The latter is employed as racemate essentially for the treatment of acute and chronic liver disorders and in cases of poisoning. Since only the natural R-(+)-α-enantiomer displays biological activity, asymmetric synthesis of this pure natural substance is very important.

The novel process for preparing the compounds I is distinguished from the prior art by being straightforward to carry out and providing good yields of products of high purity, because the compounds IIa are novel starting materials for synthesizing the compounds I.

The present invention makes it possible to obtain the physiologically important R-(+)-α-liponic acid in a straightforward and economic manner and in high optical yield.

The compounds II are prepared according to the invention from the compounds III, and, in particular, the novel compounds IIIb provide high optical yields of the compounds II.

EXAMPLES

Examples 1 To 6

A) Preparation of (3S)-3-hydroxyoctanedioic diesters of the formula

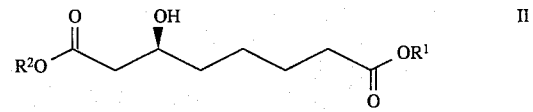

42 g of dry baker's yeast were added to a solution of 20 ml of ethanol (abs.) in 1000 ml of water, and the mixture was heated to 35° C. over the course of 0.5 hour. Then 10 g of compound III were added, and the solution was stirred at 36° C. for a further 24 to 72 hours.

The yeast was separated off and washed first with 150 ml of water and then with 450 ml of hexane. After extraction with 800 ml of hexane, the extract was washed with sodium bicarbonate and finally dried.

The details of these experiments and their results are to be found in the table which follows.

Example 7

B) Preparation of methyl (6S)-6,8-dihydroxyoctanoate 100 mmol of sodium borohydride were added to a solution of 50 mmol of 1-isobutyl 8-methyl (3S)-3-hydroxyoctanedioate in 100 ml of tetrahydrofuran, and the resulting suspension was heated at 65° C. for 2 hours.

The solution was cooled to room temperature and then neutralized with 200 ml of saturated sodium bicarbonate solution, subsequently extracted with 400 ml of ethyl acetate and finally dried. The residue was redissolved in 150 ml of methanol, and the solution was then heated at 64° C. for 2 hours. The methanol was removed and the product was finally dried.

The product I was obtained in a yield of 88% and with an enantiomer ratio of 97:3.

TABLE

Preparation of (3S)-3-hydroxyoctanedioic diesters II

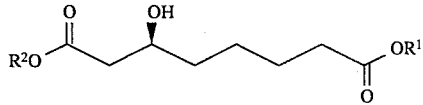

| Example | $R^1$ | $R^2$ | Yield of II [%] | Enantiomer ratio |
|---------|-------|-------|-----------------|------------------|
| 1 | methyl | methyl | 45 | 85:15 |
| 2 | methyl | iso-propyl | 70 | 60:40 |
| 3 | methyl | n-butyl | 65 | 65:35 |
| 4 | methyl | iso-butyl | 70 | 97:3 |
| 5 | methyl | sec-butyl | 60 | 65:35 |
| 6 | methyl | iso-pentyl | 55 | 70:30 |

We claim:

1. A (3S)-3-hydroxyoctanedioic diester of the formula II

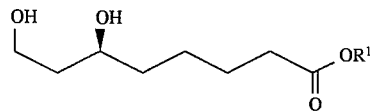

where $R^1$ is methyl and $R^2$ is isobutyl, wherein the enantiomer ratio of said diester is at least 60%.

2. A process for preparing a (6S)-6,8-dihydroxyoctanoic ester of the formula I

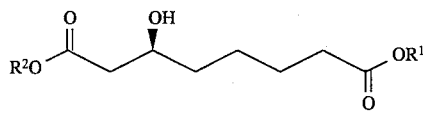

where
$R^1$ is $C_1$–$C_5$-alkyl, $C_3$–$C_8$-cycloalkyl, phenylethyl, benzyl, naphthyl and phenyl, which comprises reducing a (3S)-3-hydroxyoctanedioic diester of the formula II

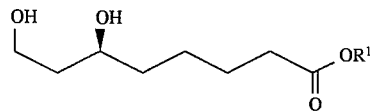

where $R^2$ is one of the $R^1$ radicals, with a complex hydride.

3. A process as defined in claim 2, wherein sodium borohydride is used as complex hydride.

4. A process as defined in claim 2, wherein the reduction is carried out in an aprotic solvent.

5. A process as defined in claim 2, wherein tetrahydrofuran is used as aprotic solvent.

6. A process for preparing R-(+)-α-liponic acid of the formula IV

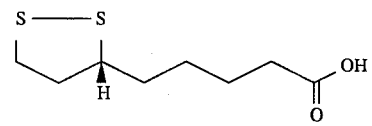

which comprises reducing a compound II as defined in claim 2 to a compound I and, a) converting the latter in organic solution with a sulfonyl chloride and a tertiary nitrogen base into the bissulfonic ester of I,
b) reacting this compound in a polar solvent with sulfur and an alkali metal disulfide to give an R-α-liponic ester and
c) optionally converting this ester into physiologically tolerated R-(+)-α-liponic acid.

7. A process as defined in claim 6, wherein in the compound II $R^1$ is methyl and $R^2$ is isobutyl.

* * * * *

UNITED STATES PATENT AND TRADEMARK OFFICE
CERTIFICATE OF CORRECTION

PATENT NO.: 5,530,143

DATED: June 25, 1996

INVENTOR(S): BALKENHOHL et al.

It is certified that error appears in the above-identified patent and that said Letters Patent is hereby corrected as shown below:

On the cover page, item [30], the foreign priority application data "40 37 440.8" should read --P 40 37 440.8--.

Signed and Sealed this

Seventeenth Day of September, 1996

Attest:

BRUCE LEHMAN

Attesting Officer

Commissioner of Patents and Trademarks